United States Patent [19]

Beggs et al.

[11] Patent Number: 5,434,087
[45] Date of Patent: Jul. 18, 1995

[54] FOLATE IMMUNOASSAY UTILIZING FOLATE BINDING PROTEIN IN A MULTICLONAL ANTIBODY FORMAT

[75] Inventors: Michael J. Beggs, Waukegan; Linda J. Sohn, Palatine; Robert J. Herrmann, Gurnee; Stephen Hsu, Vernon Hills; David J. Hawksworth, Mundelein; Mary S. Pinkus, Chicago, all of Ill.

[73] Assignee: Abbott Laboratories, Abbott Park, Ill.

[21] Appl. No.: 21,942

[22] Filed: Feb. 24, 1993

[51] Int. Cl.⁶ ............ G01N 33/567; G01N 33/543; G01N 33/537; G01N 33/539
[52] U.S. Cl. .................. 436/505; 436/518; 436/538; 436/539; 435/7.21; 435/7.93; 435/7.94; 435/971; 530/391.1
[58] Field of Search .......... 435/7.21, 7.93, 70.21, 435/240.27, 962, 967, 971; 436/505, 518, 538, 539, 548, 815; 530/388.22, 391.1

[56] References Cited

U.S. PATENT DOCUMENTS

| | | | |
|---|---|---|---|
| 4,028,465 | 6/1977 | Lewin et al. | 436/505 |
| 4,146,602 | 3/1979 | Gutcho et al. | 424/1.69 |
| 4,188,189 | 2/1980 | Allen | 23/230.3 |
| 4,271,140 | 6/1981 | Bunting | 436/500 |
| 4,350,659 | 9/1982 | Riceberg | 422/61 |
| 4,351,822 | 9/1982 | Allen | 424/1.73 |
| 4,399,228 | 8/1983 | Riceberg | 436/505 |
| 4,418,151 | 11/1983 | Forand et al. | 436/505 |
| 4,423,154 | 12/1983 | Gutcho et al. | 436/505 |
| 4,451,571 | 5/1984 | Allen | 436/505 |
| 4,517,288 | 5/1985 | Giegel et al. | 435/5 |
| 4,828,985 | 5/1989 | Self | 435/7.9 |
| 4,950,612 | 8/1990 | Khanna et al. | 436/505 |
| 5,011,771 | 4/1991 | Bellet et al. | 435/7.94 |
| 5,244,630 | 9/1993 | Khalil et al. | 422/54 |

FOREIGN PATENT DOCUMENTS 9314405 7/1993 WIPO .

OTHER PUBLICATIONS

Hoier—Madsen, M. et al, Biosci Rep 7(7): 553-7 Jul. 1987 (Abstract only).
Payne, W. J. et al, Clin Micro Rev 1(3): 313-29 Jul. 1988.

Primary Examiner—Toni R. Scheiner
Assistant Examiner—Nancy J. Parsons
Attorney, Agent, or Firm—David L. Weinstein

[57] ABSTRACT

An improved method for performing immunoassays whereby specific binding proteins for vitamin B12, folate and other target analytes are utilized with antibodies with different specificities for the binding proteins. Antibodies bridge the specific binding protein directly or indirectly to a capturable material.

25 Claims, 2 Drawing Sheets

FOLATE IMMUNOASSAY UTILIZING FOLATE BINDING PROTEIN IN A MULTICLONAL ANTIBODY FORMAT

BACKGROUND OF THE INVENTION

1. Field of the Invention

This invention relates to specific binding assays in which binding proteins specific for a sample analyte are bound by antibodies. The antibodies are specific for different epitopes of the binding protein and can be attached to either soluble or insoluble materials which facilitate separation procedures.

2. Description of the Prior Art

This invention relates to methods and means for determining the presence of a ligand in a liquid medium based on the affinity of the ligand for a specific binding partner. In particular, this invention relates to methods and means for use in specific binding assays which do not employ radioactive materials.

Folate deficiences in the human body are a common cause of megaloblastic anemia. In humans, folic acid is metabolized to tetrahydrofolic acid and subsequently to 5-methyltetrahydrofolic acid (5'-mTHF). Often, the concentration of 5'-mTHF is measured using a competitive binding assay. It would be useful to include 5'-mTHF used in the standard reagents as a calibrator. Unfortunately, 5'-mTHF is very unstable and its use can require sealing the material in lyopholized form.

U.S. Pat. No. 4,350,659 to Riceberg of Corning Glass Works disclosed a process for stabilizing 5'-mTHF by complexing it with a binding protein such as folate binding protein (FBP). The complex is then frozen and lyophilized to yield a dry powder. Recommended storage of the powder includes air tight and light resistant containers. Lypholization permits storage of 5'-mTHF in a stable form until it is needed. Such techniques are impractical in the manufacture of assay kits and make it difficult to use in clinical laboratory settings. Moreover, after reconstituting the lypholized material, instability problems can reappear.

Deficiencies in vitamin $B_{12}$ may result in neurological damage. Futhermore, as this vitamin is necessary for proper folic acid metabolism, its absence also results in megaloblastic anemias. Since megaloblastosis may also be produced by folate deficiency due to other causes, it is necessary to determine if the megaloblastosis is caused by a deficiency of either or both vitamins.

U.S. Pat. No. 4,399,228 to Riceberg of Corning Glass Works discloses a folate and vitamin $B_2$ competitive protein binding assay. Radioactive $^{57}Co$ or $^{125}I$ tracer is added to patient samples and counted with a gamma counter. In the assay, the binding protein is covalently bound to porous glass. The endogenous binding proteins in the patient sample are destroyed by boiling the reaction tube. Because of the hazard and difficulty of handling radioactive materials, there have been many attempts to devise convenient specific binding assay systems which are as sensitive and rapid as radioimmunoassays but which utilize features other than radioactivity as the means for monitoring the binding reaction.

U.S. Pat. No. 4,028,465 to Lewin et al., of Bio-Rad Laboratories discloses a radioactive competitive assay procedure where sample serum folate is measured. The serum folate binding proteins are inactivated by heat. The invention discloses the use of a sulfhydryl such as dithiothreitol in buffer which can be used to stabilize folate prior to the heating process. The use of this stabilizer was advantageous over methods utilizing mercaptoethanol because it is an easily weighed solid with only a mild odor.

Folate and vitamin $B_{12}$ assays typically employed heating or boiling steps prior to testing in order to liberate folate in the sample from endogenous binding proteins. The heating or boiling steps are difficult to accurately control and are time consuming. More recent assays denature samples by chemical means without boiling. One can achieve denaturation by using a strong base with or without other chemicals.

U.S. Pat. No. 4,418,151 to Forand et al., of Rohm and Haas Company also relates to a radioassay for serum folate. A measured amount of serum is mixed with a constant amount of radioactively tagged vitamin B12 and/or folate tracer. The solution is exposed to a mercaptan denaturing agent in the presence of a conversion agent such as potassium cyanide in a highly alkaline environment. The use of mercaptan solutions allows stabilization in the protecting buffer while high pH causes inactivation of the endogenous binding proteins.

U.S. Pat. No. 4,451,571 to Allen of University Patents teaches the use of strong base with a sulfhydral compound, such as betamercaptoethanol (BME), thioglycolate, thioglycerol or dithiothreitol (DTT). The sulfhydral compounds destroy endogenous binding proteins thereby liberating the sample vitamin $B_{12}$ or folate to be measured. Although the strong base releases analyte from its binding protein, it does not substantially denature all endogenous binding protein. Therefore it is helpful to have another compound such as a sulfhydral to help liberate analyte from binding protein and also eliminate blocking antibodies which may interfere in the assay. The blocking antibodies can be troublesome to the assay because they react with binding factors.

U.S. Pat. No. 4,828,985 to Self of Cambridge Patent Developments teaches a method where secondary antibodies are raised against complexes of nonimmunogenic materials and primary antibodies against the nonimmunogenic materials. The secondary antibodies are not antibodies against either the nonimmunogenic materials nor the primary antibodies. Detection is accomplished by labelling the secondary antibodies with enzyme or some other detectable means.

The present invention is an improvement over existing technology in that it discloses a method that enables more coupling of specific binding proteins. This invention discloses a method whereby a mixture of two monoclonal or polyclonal antibodies or a mixture thereof against different epitopes of a binding protein gives increased coupling. This method can be utilized for several different assays in which analyte is detected. Another advantage of the present invention is that this multiclonal format allows the use of pteryolglutamic acid (PGA) as a calibrator in a folate assay instead of the unstable 5'-mTHF.

SUMMARY OF THE INVENTION

The present invention relates to a method of a heterogenous assay whereby the ability to bind specific binding proteins is enhanced with a multiclonal antibody format. The multiclonal format couples binding proteins up to ten times the efficiency of a singular antibody format. The improved method generally comprises directly or indirectly binding a specific binding pair member to a capturable material by utilizing a mixture of antibodies. The specific binding pair member contains binding sites which will then be occupied by either the sample analyte of interest or a labelled analyte analog. A capturable material, one in which the antibodies, specific binding pair members and sample analyte or analyte analog are attached, can then be isolated by ionic interactions with a matrix material where detection can take place.

This invention can be utilized for any assay employing binding proteins which can couple specific ligands. Another advantage of the present invention is the use of PGA as a calibrator in a folate assay instead of 5'-mTHF. Traditional use of 5'-mTHF in folate assays has proved it to be an unstable compound. The use of the present invention allows PGA to be used as a calibrator whereas a monoclonal or polyclonal format alone exhibited differential performance between PGA and 5'-mTHF.

DETAILED DESCRIPTION OF THE INVENTION

Multiclonal Format

Figure 1:
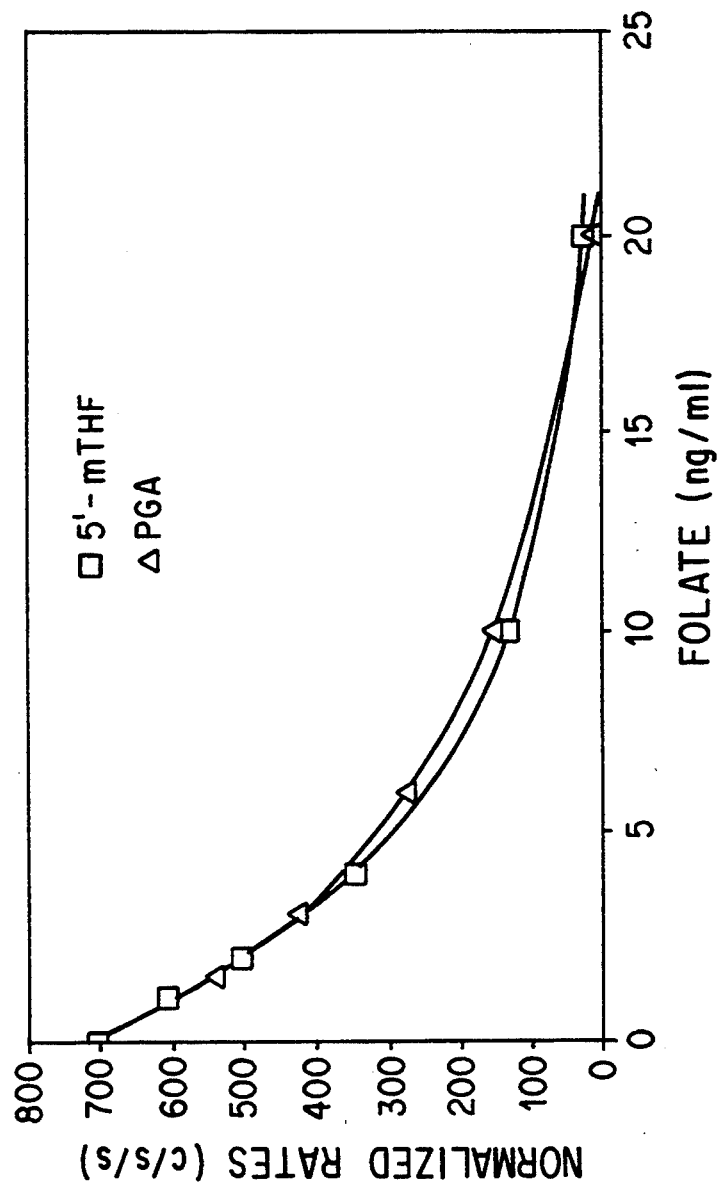
FIG. 1 shows folate binding protein binding PGA similarly to 5'-mTHF in the multiclonal format.

This invention relates to methods and means for determining the presence of a ligand in a liquid medium based on the affinity of the ligand for a specific binding protein.

The present invention discloses a method of a heterogenous assay for measuring analytes in patient samples. There are two separate phases to this procedure. The first phase is the coupling of a polyanionic substance to antibodies with different binding specificities for a particular binding protein. The binding protein is then added to the antibodies creating a polyanion:anti-binding protein antibody:binding protein complex. This complex is referred to as a capture reagent. The second phase is the reaction of particular reagents with the patient sample. The binding protein in the complex captures its particular analyte in the patient sample. The reaction mixture is transferred to a polycation matrix where the polyanion is caught. A reagent containing an analyte analog coupled to an enzyme is added to bind to any unoccupied binding proteins. Non-bound materials are washed away from the matrix and after addition of a standard fluorescent substrate for the enzyme, analyte concentration can be determined from fluorescent intensity.

The present invention also employs a method in which a mixture of two or more anti-binding protein monoclonal or a mixture of monoclonal and polyclonal antibodies works better than a single antibody alone. One example of how this method can work is folate binding protein (FBP). The two or more antibodies (two or more monclonal or a mixture of monoclonal and polyclonal antibodies) are attached to a polyanion such as carboxymethylamylose (CMA) through covalent linkage. FBP is then added to the mixture and the FBP is coupled non-covalently to the antibodies. In effect, the antibodies act as a linker between the FBP and the polyanion. This method prevents having to directly link the binding protein to the polyanion. Direct linkage of the binding protein to the polyanion could conformationally change the binding protein thereby affecting its ability to bind test sample analyte. To show the marked difference when two antibodies are used as opposed to a single monoclonal, two individual monoclonal antibodies were tested against a 1:1 mixture of the two antibodies. In the competitive assay described above, the FBP was linked to the CMA by one or both monoclonal antibodies. The 1:1 mixture of the two anti-FBP monoclonals works better than either monoclonal alone. Table 1 gives an indication as to how effective the multiclonal format is. The numbers in Table 1 refer to the substrate turnover rate. It is important to note that this format uses antibodies that have different affinities to the same protein.

TABLE 1

| [FLOATE] | CLONE A (c/s/s) | CLONE B (c/s/s) | 1:1 MIXTURE |
|---|---|---|---|
| 0 ng/ml | 370 | 687 | 2342 |
| 4 ng/ml | 206 | 337 | 1412 |
| 30 ng/ml | 32 | 48 | 141 |

The 1:1 mixture of the two antibodies gave a dramatically increased signal. This indicates that there is more folate binding protein bound by the antibodies in the 1:1 mixture. This in turn means more coupling of analyte analog and hence more signal.

The coupling of antibody to the polyanion can be achieved in one of two ways. First, the individual monoclonals or mixture of monoclonal and polyclonals can be coupled at separate times. Therefore, each of the antibodies is coupled to the polyanion in a separate incubation step before being mixed in a 1:1 fashion. The second method is to mix both antibodies together (using appropriate ratios of antibodies) and then couple the mixture to the polyanion in a single incubation step. The second method is useful when working with large quantities of antibody because of the single incubation time.

Different ratios of monoclonal antibodies give better results with the multiclonal format than the individual clones alone. Apparently, even minor additions of a multiclonal format yield increased anti-binding protein antibody:binding protein capabilities. Results of experiments utilizing the monoclonal versus multiclonal format and varying ratios of the multiclonal format are presented in Table 2. Once again, values presented are substrate turnover rate due to detectable label binding to unoccupied binding protein sites.

TABLE 2

| % of Clone A | % of Clone B | 0 ng/ml Folate | 4 ng/ml Folate | 20 ng/ml Folate |
|---|---|---|---|---|
| 100 | 0 | 447 | 245 | 43 |
| 80 | 20 | 2479 | 1581 | 170 |
| 70 | 30 | 2551 | 1640 | 178 |
| 50 | 50 | 2461 | 1571 | 172 |
| 30 | 70 | 2403 | 1487 | 168 |
| 0 | 100 | 640 | 360 | 50 |

Characterization of Folate Binding Protein Antigen

FBP antigen was isolated from bovine whey by PGA affinity chromatography. Silver-stained polyacrylamide gel electrophoresis (PAGE) and isoelectric focusing verified the homogeneity of the protein. Two bands visible by PAGE corresponded to the published molecular weights of bovine FBP with and without glycosylation. Cation and anion exchange chromatography, as well as reverse phase high performance chromatography methods, showed no more than two entities in the FBP preparation. Chemical deglycosylation with trifluoromethanesulfonic acid converted the higher molecular weight component into a single entity with an electrophoretic mobility identical to the lower molecular weight band. These data support the conclusion that the two components represent FBP with different degrees of glycosylation.

Additional verification that the protein was FBP was provided by the following: 1) the protein exhibited specific, high affinity binding of radioactive folate, 2) N-terminal amino acid sequence analysis of the first twenty three amino acids provided an unambiguous sequence in perfect agreement with the amino acid sequence published for bovine FBP (Svendsen, I., Hansen, S. I., Holm, J., and Lyngbye, J., Carlsberg Research Communications, 49:12–31, 1984), and 3) gas chromatography mass-spectroscopy analysis showed two components with molecular masses of 30,850 and 25,968 consistent with the expected mass of the FBP polypeptide with and without carbohydrate side chains.

FBP Monoclonal Antibody Development

Immunogen Preparation

Purified folate binding protein (FBP) was used as the immunogen for animal immunizations and the antigen for reactivity screening.

Immunization Strategy

Two female 6–8 week old BALB/c mice (Charles River, Wilmington, Mass.) were immunized with purified folate binding protein (FBP). The dose level was 200 $\mu$g in 100 $\mu$l of a 1:1 ratio of the FBP solution in Freund's Complete Adjuvant (Difco Laboratories, Detroit, Mich.). The adjuvant emulsion route of injection was equally distributed interperitoneally and subcutaneous. The animals were allowed a 3 week rest period before a 100 $\mu$g FBP intravenous prefusion boost was administered in 100 $\mu$l, 3 days prior to fusion.

Fusion

On the day of the fusion, the 2 mice were sacrificed by cervical dislocation and the spleen was removed. The splenocytes were washed one time in Iscove's Modified Dulbecco's Medium (IMDM) (GIBGO, Grand Island, N.Y.) and centrifuged 1000 RPM for 10 minutes. The pelleted splenocytes were combined with SP2/O myeloma cells (from the laboratory of Dr. Milsrein, Cambridge, U. K.) at a 1:1 ratio, washed in IMDM, and centrifuged. The supernatant was removed and 1 ml of 50% polyethylene glycol (PEG) (American Type Culture Collection, Rockville, Md.) was added to the pellet for 1 minute as the pellet was gently being dispersed by tapping and swirling. Thirty mls of IMDM were added to the mixture and centrifuged as previously described. The supernate was decanted and the pellet resuspended in IMDM with HAT (hypoxanthine, aminopterin, and thymidine) (Gibco, Gaithersburg, Md.), 10% Fetal Bovine Serum (FBS) (Hyclone Laboratories, Logan, UT.) and *Salmonella typhimurium* mitogen (STM) (1% v/v) (RIBI Immunochem Research, Inc., Hamilton, Mont.). STM is a B-cell specific mitogen, and is used to enhance fusion frequency. The fusion cell suspension was plated into 96-well tissue culture plates.

Primary Fusion Screening

The primary screening of the fusion occurred on day 10 at which time the cultures were confluent. An enzyme immunoassay (EIA) was used to detect anti-FBP reactivity in the supernate samples. Microtiter wells were coated with 100 $\mu$l of a 5 $\mu$g/ml FBP in phosphate buffered saline (PBS) and incubated at room temperature overnight. The following day the plates were blocked for 30 minutes with 200 IL1 per well of 3% bovine serum albumin (BSA) in PBS. After washing the plates 3 times with distilled water, 50 $\mu$l of culture supernate was added per well and incubated 1 hour. The plates were washed 3 times and 50 $\mu$l per well of diluted goat anti-mouse IgG+IgM-HRPO (horseradish peroxidase) conjugate (Kirkegaard Perry Laboratories, Gaithersburg, Md.) was added to the plate for a 30 minute incubation period. The plate was washed a final time and the color development utilized O-phenylenediamine:2HCI (OPD) (Abbott Laboratories, Abbott Park, Ill.). The relative intensity of optical density readings identified hybrids #1-279 and #1-641 as 3 times that of the negative control, normal mouse serum (NMS) (Organon Teknika-Cappel, Malvern, Pa.) and the hybrids were selected as candidates for cloning and further evaluation.

Hybrid Cloning

Hybrids #1-279 and #1-641 were cloned by limiting dilutions. 1 to 10 dilutions were done starting at $1\times10^2$ up to $1\times10^6$. The cloning media used was IMDM with 10% v/v FBS and 1% v/v HT (hypoxanthine and thymidine)Supplement (Gibco, Gaithersburg, Md.). A 100 $\mu$l cell suspension was added to each of the 96 well in the TC plate. On day 7 the plates are fed with 200 $\mu$l/well of cloning media.

Clone Selection

Clones #1-279-176 and #1-641-101 were selected from the $1\times10^6$ dilution wells for further evaluation based on additional EIA screening of the clone supernate of confluent cultures. The EIA screening protocol used is described previously.

Subclone Selection

For purposes of reagent reproducibility it was necessary to ensure that a single cell line of 1-279-176 was obtained. To do so, the cell line was cloned one more time as described above. EIA screening as described above was used for subclone selection of #1-279-866.

Western Blot Evaluation

The FBP antigen, 10 $\mu$g, either reduced with 2-mercaptoethanol (Bio-Rad, Richmond, Calif.) or non-reduced was run on an 8–16%, 1.0 mm, mini-polyacrylamide gel (Novex, San Diego, Calif.) on a mini electrophoresis and transfer system (Profile TM System, Schleicher & Schuell, Keene, N.H.) according to manufacturer's instructions. The protein was next transferred from the gel onto nitrocellulose. The nitrocellulose was cut into strips and antibody was incubated on the strips for several hours. The antibody binding capability to the reduced and non-reduced antigen was detected using the goat anti-mouse IgG+M-HRPO conjugate mentioned above with the color development driven by 4-chloro-napthol (Sigma, St. Louis, Mo.). Antibody from 1-279-866 was found reactive to the 32kD MW FBP in reduced and non-reduced conditions. Antibody from 1-641-101 was not found reactive to FBP antigen in the Western blot test. Based on these data, the monoclonal antibody produced by the hybrid cell lines were determined to be directed against two distinct epitope binding sites.

Isotype

The isotypes of the monoclonal antibody secreted from the cell lines identified as 1-279-866 and 1-641-101 were determined on an EIA clonotyping kit (Southern Biotech, Birmingham, Ala.). The assay is performed according to the vendor recommendations and the results indicate that both were IgG1, kappa.

Isoelectric Focusing

Electrophoretic evaluation of the 1-279-866 and 1-641-101 antibodies was performed on the PhastSystem (Pharmacia-LKB, Piscataway, N.J.). Coomassie staining of the sodium dodecyl sulfate polyacrylamide gel electrophoresis (SDS-PAGE) profile identified the typical antibody banding pattern of a single light chain band at 25 kD and a single heavy chain band at 55 kD for each antibody. The silver stained IEF profile identified a pI of 6.8±0.2 for 1-279-866 and a pI of 6.6±0.2 for 1-641-101.

Deposit

Cell lines 1-279-866 and 1-641-101 have been deposited with the American Tissue Culture Collection (A.T.T.C on Jan 26, 1993) (16301 Parklawn Drive Rockville, Maryland). Cell line 1-279-866 has been designated A.T.C.C No. HB 11249 and cell line 1-641-101 has been designated A.T.C.C No. HB 11250.

Methods and Reagents

The current invention teaches a method wherein a mixture of two or more anti-binding protein monoclonal or a mixture of monoclonal and polyclonal antibodies gives a better reaction rate than either monoclonal or polyclonal alone. This method of assay is applicable for many proteins and their binders including folate and vitamin $B_{12}$ but is not limited to them.

The sample to be tested for the presence of analyte can be subject to various steps that denature endogenous proteins which may interfere with the assay. The present invention preferably employs a pretreatment of the sample with the DTT mixed with acetic acid, sodium chloride, and ethyldiaminetetraacetic acid (EDTA). The DTT not only denatures protein but also preserves the reduced form of 5'-mTHF. Other general denaturing agents may substitute for DTT depending on the analyte.

A second denaturing step is preferably the addition of 0.75M potassium hydroxide to the sample. This addition creates a highly basic environment that further denatures the endogenous folate binders in the sample thereby releasing the folate for measurement. Other strong bases such as NaOH, LiOH and $NH_4OH$ can be used.

The capture technique employed utilizes a polyanion such as CMA. Coupled to the polyanion is a mixture of anti-folate binding protein antibodies complexed with folate binding protein. The antibodies act as linkers between the polyanion and the folate binding protein. The folate binding protein binds non-covalently to the antibodies associated with the polyanion. It is important that the denatured sample be neutralized by buffer before or at the time of addition of FBP. In the present invention, the neutralizing is preferably done at the time of FBP addition. The capture reagent may be diluted into a buffer of 50 mM borate, pH 8.1; 0.2% human serum albumin (HSA); 0.1% tween-20; 0.1% sodium azide; 0.003% dextran sulfate; and 1 mM EDTA. The HSA component contains no endogenous folate binding protein. Sodium azide is a preservative commonly used in laboratory reagents which can provide some antibacterial action. Dextran sulfate in the capture reagent binds to stray cations (i.e. cation dust from the matrix) which could interfere in the accuracy of the assay.

The addition of the capture reagent, which contains borate buffer, to the reaction well neutralizes the denaturants and allows the folate in the samples to bind to the folate binding protein. After an incubation, the reaction mixture is transferred to the matrix where the polyanion adheres to a polycation material.

There are various ways that the polycation can be added. The polycation material can be added directly to the capture reagent where it will adhere to the polyanion. Another method is to add the polycation to the reaction mixture one step prior to the reaction mixture being added to the matrix. The preferred method is to precoat the matrix with polycation and then add the reaction mixture.

The conjugate reagent contains the enzyme alkaline phosphatase conjugated to pteroic acid and diluted into 50mM Tris(hydroxymethyl)aminomethane (TRIS), pH 7.4; 0.5% HSA; 0.1M sodium chloride; 1 mM magnesium chloride; 0.1 ram zinc chloride; 0.1% dextran sulfate; and 0.1% sodium azide. The conjugate binds to the unoccupied folate binding protein sites. The conjugate reagent is not limited to the use of pteroic acid. Other folate analogs including PGA can be used in the conjugate reagent.

The standard IMx ® (Abbott Laboratories, North Chicago, Ill., 60064) methylumbelliferyl phosphate substrate is used in the present invention.

As mentioned earlier, there have been problems in using 5'- mTHF as a standard or calibrator. It is unstable once exposed to light, temperature and atmosphere. Its instability negates its usefulness as a calibrator. Moreover, 5'-mTHF may necessitate using human serum in the calibration matrix. Also necessary when using 5'-mTHF is the addition of ascorbate and citrate. The addition of these increases the stability of 5'-mTHF during usage but ascorbate was found to interfere in the assay.

The present invention uses PGA as its calibration reagent. The advantages of using PGA are several. First, PGA is more stable than 5'-mTHF; second,there is better reproducibility of results with PGA calibrating the assay over 5'-mTHF; and third, ascorbate is not needed to stabilize PGA. Additionally, PGA as a calibrator allows the use of bovine serum albumin (BSA) instead of human serum as the calibrator diluent. This lessens the hazards, cost and availability problems associated with human serum.

5'-mTHF is the metabolic form of folic acid that is actually measured in patient samples. Accordingly, calibrators other than 5'mTHF must be sufficiently bound by the appropriate binding proteins to give good correlation to sample 5'-mTHF levels. Although the mechanism by which it works is unknown, the multiclonal format allows FBP to bind PGA in a similar fashion to that of 5'-mTHF. Therefore, the multiclonal format allows calibration with PGA and gives a good indication of test sample 5'-mTHF. An example of the comparison is given in FIG. 1.

Figure 2A:
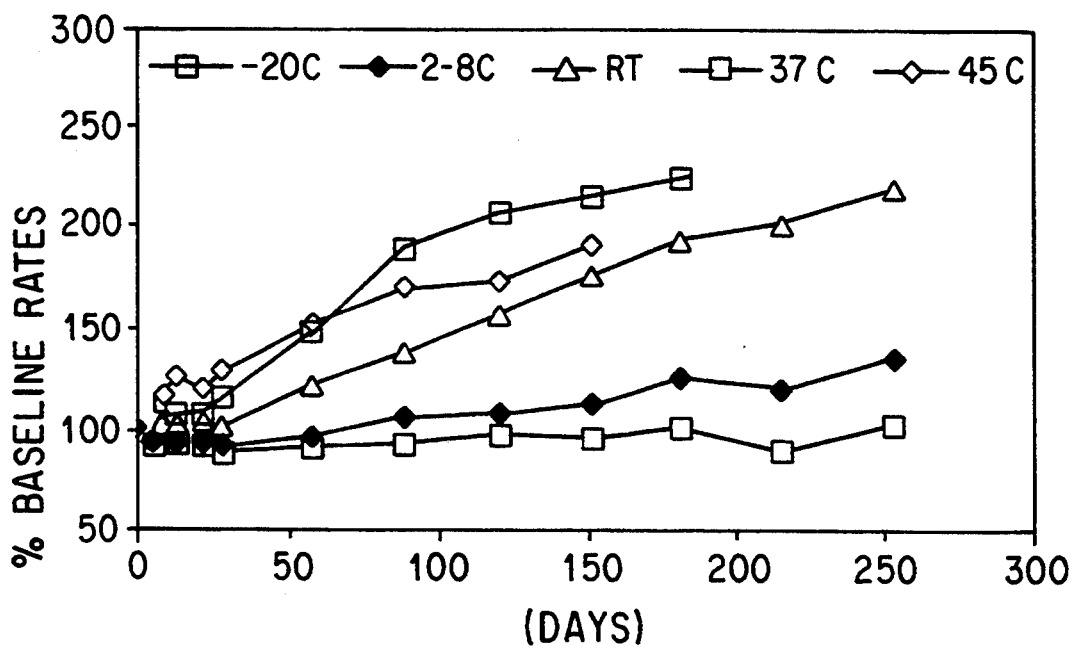
FIG. 2A shows the effects of not adding citrate
Figure 2B:
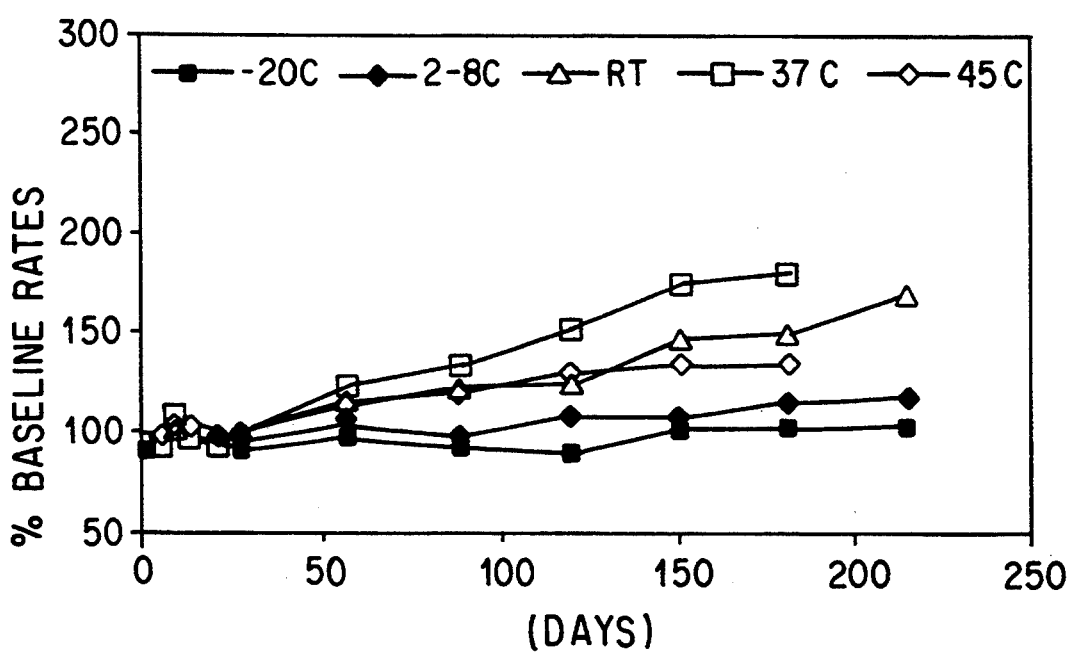
FIG. 2B shows the effects of adding citrate for increased PGA stability.

Another improvement of the present invention is the finding that addition of citrate improved PGA stability of day zero values to several months. PGA day zero value stability was evaluated in the BSA diluent with and without citrate (100 mM). With citrate, PGA day zero value stability is improved over time at −20° C., 4° C., 45° C., and room temperatures. FIG. 2B shows the effects of citrate enhanced PGA day zero value stability over no citrate addition (FIG. 2A). Test points were run the IMx ® instrument and MUP turnover rates were measured on the days indicated. The rates obtained were compared to the baseline runs of day zero.

The same methodology can be used to assay for vitamin B12. Vitamin B12 is preferably separated from its endogenous intrinsic 5 factor with the use of alpha-methyl thioglycerol and subsequent high alkaline enviroment. This allows the released vitamin B12 to couple to the capture reagent complex, thereby facilitating the detection process.

Patient samples were analyzed and individual folate concentrations were measured using two commonly used assays. Patient samples were analyzed by the IMx ® against Bio-Rad ® (Bio-Rad Chemical Div. Richmond, Calif., 94804) and Corning ® (Corning Inc., Science Products Division, Corning, N.Y., 14831) assays with both the multiclonal and polyclonal format. As can be seen in Table 3, there was good agreement between the two methods. The designation "N" refers to the number of patient samples tested.

TABLE 3

|  | Mutliclonal | Polyclonal |
|---|---|---|
| IMx ® v. Bio-Rad ® | | |
| Intercept | 0.84 | 1.14 |
| Slope | 0.67 | 0.57 |
| R value | 0.98 | 0.98 |
| N | 47 | 47 |
| IMx ® v. Corning ® | | |
| Intercept | 0.87 | 1.40 |
| Slope | 0.61 | 0.50 |
| R value | 0.94 | 0.92 |
| N | 46 | 46 |

Also significant is the fact that the multiclonal reagent showed good stability after 3 days at 45° C. Two individual monoclonals, a 1:1 mix of the two monoclonals, and a polyclonal sample were tested at the different temperatures. The multiclonal reagent (1:1 mix) lost only 10% of its 4° C. activity after 3 days at 45° C. As shown in Table 4, the multiclonal format shows good ability to bind more binding protein as indicated by higher substrate turnover rates after storage at higher temperatures.

TABLE 4

| [Folate] | Clone A | Clone B | 1:1 Mix | Polyclonal |
|---|---|---|---|---|
| Day 3-4 Degree | | | | |
| 0 ng/ml | 906 | 1274 | 2245 | 982 |
| 4 ng/ml | 646 | 835 | 1184 | 567 |
| R4/R0 | 0.71 | 0.66 | 0.53 | 0.58 |
| Day 3-45 Degrees | | | | |
| 0 ng/ml | 785 | 1025 | 2020 | 903 |
| 4 ng/ml | 565 | 686 | 1061 | 509 |
| R4/R0 | 0.72 | 0.67 | 0.53 | 0.56 |
| % activity remaining | 87 | 80 | 90 | 92 |

The present invention's methodology can be used to adapt it to several analytes. The antibodies used were developed to aide in eliminating reagent performance variability. The multiclonal format was initially prepared by mixing two of the CMA-antibody conjugates together in the capture reagent. This was later simplified by mixing the two antibodies together and then coupling the mixture to CMA to generate a multiclonal. The antibody mixture can be two separate monoclonal or a combination of monoclonal and polyclonal antibodies.

DTT reagent is added to samples at the beginning of the assay to maintain a reducing environment for preserving sample 5'-mTHF. DTT can also function as a protein denaturant by reducing disulfide bonds and making other proteins more susceptible to alkaline denaturation. Published articles have indicated that folate binding proteins are irreversibly denatured at a pH of 12 or greater. The present invention preferably uses a potassium hydroxide reagent to denature patient samples by destroying endogenous folate binding proteins. This allows the CMA-multiclonaI-FBP complex to bind with the released patient sample folate. Thus, the assay must reproducibly raise the pH for denaturation and then neutralize the base with the capture diluent. Current literature and our experience suggests that a pH of approximately 9.3 gives optimum binding of PGA in the calibrators and the 5'-mTHF in the samples. In the present invention, not only must the diluent be appropriate for the CMA-multiclonaI-FBP capture reagent to 0 function and remain stable but it must also neutralize the KOH. The capture reagent therefore buffers the reaction pH for appropriate PGA and 5'-mTHF performance. Borate is a preferable buffer with a pKA near 9.3 and is conducive for FBP binding ability. Addition of 4% sucrose increases the solubility of borate. The ability of sucrose to 5 perform this function is due to the cis-hydroxy groups which combine with the borate. Sucrose prevents the occasional precipitation of borate from capture diluent stored at 4° C.

Folate Assay

1. Procedure
   a. Load the IMx ® (Abbott Laboratories, Abbott Park, Ill., 60064) carousel with the calibrators and/or controls and test samples (minimum of 100 ul each). Then 0.4 ml of dithiothreitol (DTT) is placed into the predilute well of the first reaction cell in the carousel.
   b. The assay begins with each reaction well receiving 0.015 ml of the DTT from the first reaction cell's predilute well and 0.018 ml of the calibrator, control, or sample. The DTT denatures proteins and preserves the reduced form of 5'-mTHF in the samples. Each well is incubated for 8 minutes.
   c. Add 0.028 ml of the 0.75M potassium hydroxide (KOH) into each reaction well and incubate 8 minutes.
   d. Add 0.15 ml of capture reagent (polyanion-anti-FBP antibody complexed with FBP in borate buffer) to the reaction well. The borate buffer in the capture reagent neutralizes the denaturants (final pH near 9.3) and allows the folate in the samples to bind to the FBP. The dextran sulfate in the capture reagent binds to stray cations (i.e. cation dust from the matrix) and reduces assay variability. Incubate the wells for 12.5 minutes.

Transfer 0.22 ml of the reaction mixture to the ion capture reaction cell matrix where the polyanion (connected to the FBP through the antibodies) adheres through ionic interactions to the polycation on the reaction cell matrix.
   f. Two diluent washes of the matrix remove unbound materials and then are followed by the addition of 0.06 ml of conjugate reagent. The conjugate reagent used is calf intestine alkaline phosphatase conjugated to pteroic acid. The conjugate binds to sites on the captured FBP unoccupied by folate.
   g. Unbound conjugate is then washed from the surface of the matrix, 0.06 ml of methylumbelliferyl phosphate (MUP) reagent is added, and the fluorescence of the liberated MU is read. The fluorescence intensity is inversely proportional to the amount of folate in the calibrators or patient samples.

Vitamin $B_{12}$ Assay

1. Procedure
  a. Load the carousel with the calibrators and/or controls and test samples (minimum 100 ul each). Then 0.4 ml of alpha monothioglycerol is placed into the predilute well of the first reaction cell in the carousel.
  b. The assay begins with each reaction well receiving 0.01 ml of alpha monothioglycerol and 0.06 ml of the calibrator, control, or sample. The reducing agent denatures proteins. Incubate for 8 minutes.
  c. Add 0.08 ml of the KOH into each reaction well and incubate for eight minutes.
  d. The addition of 0.15 ml of capture reagent (polyanion-anti-intrinsic factor antibody complexed with intrinsic factor in borate buffer) to the reaction well then neutralizes the denaturants (final pH near 9.3) and allows the vitamin $B_{12}$ in the samples to bind to the intrinsic factor. The dextran sulfate in the capture reagent binds to stray cations (i.e. cation dust from the matrix) and reduces assay variability. Incubate for 12.5 minutes,
  e. 0.15 ml of the reaction mixture is transferred to the ion e. capture reaction cell matrix where the polyanion (connected to the intrinsic factor through the anti-intrinsic factor antibody) adheres through ionic interactions to the polycation coated on the matrix.
  f. Two diluent washes of the matrix are followed by the addition of 0.05 ml of conjugate reagent. The conjugate reagent used is calf intestine alkaline phosphatase conjugated to vitamin $B_{12}$ or vitamin $B_{12}$ analog. The conjugate binds to sites on the captured intrinsic factor unoccupied by vitamin $B_{12}$.
  g. Unbound conjugate is then washed from the surface of the matrix, 0.06 ml of methylumbelliferyl phosphate (MUP) reagent is added, and the fluorescence of the liberated MU is read. The fluorescence intensity is inversely proportional to the amount of vitamin $B_{12}$ in the calibrators or patient samples.

We claim:

1. A method for determining the presence or amount of folate in a test sample comprising: linking folate binding protein which specifically binds folate to a capturable material utilizing a mix of at least two different monoclonal antibodies, each antibody of said mix of antibodies binding said folate binding protein without inhibiting the folate binding protein's binding activity for said folate and without interfering with the binding of the other antibody, said antibodies being coupled to said capturable material; forming a test mixture by contacting said folate binding protein with said folate present in said test sample; adding a detectable label to said test mixture, said detectable label being either directly or indirectly attached to a specific binding member, said specific binding member specifically binding either said folate in said test sample or the folate hiding site of said folate binding protein; capturing said capturable material by ionic interaction and separating it from said test mixture; and monitoring either the free or captured detectable label for presence or amount of said folate wherein said mix of antibodies coupled to said capturable material results in an enhanced coupling of said specific binding member directly or indirectly attached to said detectable label thereby resulting in a dramatically increased signal.

2. The method of claim 1 wherein said test mixture is formed by contacting said test sample sequentially with said folate binding protein linked to said capturable material and then said detectable label attached to said specific binding member.

3. The method of claim 1 wherein said test mixture is formed by contacting said test sample simultaneously with said folate binding protein linked to said capturable material and said detectable label attached to said specific binding member.

4. The method of claim 1 wherein said mix of antibodies is provided by mixing several capturable materials, each of which has been coupled to a different antibody.

5. The method of claim 1 wherein said test sample is treated with a reducing agent followed by treatment with an alkaline agent prior to combination with said folate binding protein.

6. The method of claim 5 wherein said reducing agent is dithiothreitol.

7. The method of claim 5 wherein said alkaline agent is potassium hydroxide, sodium hydroxide, lithium hydroxide or ammonium hydroxide.

8. The method of claim 1 wherein pteroylglutamic acid (PGA) is used as a standard.

9. A method for determining the presence or amount of folate in a test sample comprising: forming a test mixture by contacting said test sample with an indicator reagent and a capture reagent, said capture reagent comprising folate binding protein linked to a polyanion polymer by a mix of at least two different monoclonal antibodies which specifically bind said folate binding protein, each antibody of said mix of antibodies binding said folate binding protein without inhibiting the folate binding protein's binding activity and without interfering with the binding of the other antibody, said antibodies being coupled to said polyanion polymer; said indicator reagent comprising a detectable label either directly or indirectly attached to a specific binding member, said specific binding member specifically binding either said folate in said test sample or the folate binding site of said folate binding protein; separating said polyanion polymer from said test mixture by ionic adherence to a matrix and monitoring either the free or captured detectable label to determine the presence or amount of said folate in said test sample wherein said mix of antibodies coupled to said polyanion polymer results in an enhanced coupling of said indicator reagent thereby resulting in a dramatically increased signal.

10. The method of claim 9 wherein said test mixture is formed by contacting said test sample sequentially with said capture reagent and then said indicator reagent.

11. The method of claim 9 wherein said test mixture is formed by contacting said test sample simultaneously with said capture reagent and said indicator reagent.

12. The method of claim 9 wherein said mix of antibodies is provided by mixing several polyanion polymers, each of which has been coupled to a different antibody.

13. The method of claim 9 wherein said test sample is treated with a reducing agent followed by treatment with an alkaline agent prior to combination with said capture reagent.

14. The method of claim 13 wherein said reducing agent is dithiothreitol.

15. The method of claim 13 wherein said alkaline agent is potassium hydroxide, sodium hydroxide, lithium hydroxide or ammonium hydroxide.

16. The method of claim 9 wherein pteroylglutamic acid (PGA) is used as a standard.

17. The method of claim 16 wherein said PGA is stabilized by the addition of citrate.

18. The method of claim 9 wherein the said specific binding member which competes with said folate is pteroic acid.

19. The method of claim 9 wherein said detectable label is alkaline phosphatase.

20. The method of claim 9 wherein said capture reagent is diluted with a borate buffer containing 4% sucrose.

21. The method of claim 9 wherein said matrix is precoated with a polycationic material.

22. The method of claim 21 wherein said polycation material is simultaneously added with said test mixture to said matrix.

23. A reagent for use in an immunoassay comprising: folate binding protein, a capturable material and a mix of antibodies wherein said folate binding protein specifically binds folate and is linked to said capturable material utilizing a mix of at least two different monoclonal antibodies, each antibody of said mix of antibodies specifically binding said folate binding protein without inhibiting the folate binding protein's binding activity for said folate and without interfering with the binding of the other antibody, said mix of antibodies being coupled to said capturable material which is captured by ionic interaction, wherein said mix of antibodies results in an enhanced coupling of an indicator reagent thereby resulting in a dramatically increased signal.

24. The reagent of claim 23 wherein said capturable material is a polyanionic material.

25. The reagent of claim 24 wherein said polyanionic material is carboxymethylamylose.

* * * * *